(12) United States Patent
Maurel et al.

(10) Patent No.: US 8,343,991 B2
(45) Date of Patent: Jan. 1, 2013

(54) ANHYDROUS CRYSTALLINE VINFLUNINE SALTS, METHOD OF PREPARATION AND USE THEREOF AS A DRUG AND MEANS OF VINFLUNINE PURIFICATION

(75) Inventors: Jean-Louis Maurel, Burlats (FR); Richard Pena, Vielmur sur Agout (FR); Jean-Paul Ribet, Mazamet (FR)

(73) Assignee: Pierre Fabre Medicament, Boulogne-Billancourt (FR)

( * ) Notice: Subject to any disclaimer, the term of this patent is extended or adjusted under 35 U.S.C. 154(b) by 545 days.

(21) Appl. No.: 12/524,898

(22) PCT Filed: Feb. 13, 2008

(86) PCT No.: PCT/EP2008/051755
§ 371 (c)(1),
(2), (4) Date: Jul. 29, 2009

(87) PCT Pub. No.: WO2008/098970
PCT Pub. Date: Aug. 21, 2008

(65) Prior Publication Data
US 2010/0029703 A1  Feb. 4, 2010

Related U.S. Application Data

(60) Provisional application No. 60/894,127, filed on Mar. 9, 2007.

(30) Foreign Application Priority Data

Feb. 13, 2007  (FR) ..................................... 07 53211

(51) Int. Cl.
*A61K 31/439* (2006.01)
*C07D 487/18* (2006.01)

(52) U.S. Cl. ...................... 514/281; 540/478
(58) Field of Classification Search ............ 540/478; 514/281
See application file for complete search history.

(56) References Cited

U.S. PATENT DOCUMENTS

| 5,620,985 A | 4/1997 | Jacquesy et al. |
| 6,127,377 A | 10/2000 | Duflos et al. |
| 2007/0155768 A1 * | 7/2007 | Leverd et al. ............... 514/283 |

FOREIGN PATENT DOCUMENTS

| EP | 1118616 | * | 7/2001 |
| FR | 512.942 A | | 2/1921 |
| FR | 2 707 988 A1 | | 1/1995 |
| FR | 2 707 988 A1 | | 1/1995 |
| FR | 2 761 990 A1 | | 10/1998 |
| FR | 2 761 990 A1 | | 10/1998 |
| WO | WO-95/03312 A1 | | 2/1995 |
| WO | WO-2007/071648 A1 | | 6/2007 |

OTHER PUBLICATIONS

Fahy et al., "*Vinca* Alkaloids in Superacidic Media: A Method for Creating a New Family of Antitumor Derivatives", J. Am. Chem. Soc., 1997, vol. 119, pp. 8576-8577, XP-002072890.

Ribet et al., " Complete assignment of $^1$H and $^{13}$C NMR spectra of vinflunine ", Magnetic Resonance in Chemistry, 2001, vol. 39, pp. 43-48.

Fahy et al., " *Vinca* Alkaloids in Superacidic Media: A Method for Creating a New Family of Antitumor Derivatives ", J. Am. Chem. Soc., 1997, vol. 119, pp. 8576-8577, XP-002072890.

Ribet et al., "Complete assignment of $^1$H and $^{13}$C NMR spectra of vinflunine ", Magnetic Resonance in Chemistry, 2001, vol. 39, pp. 43-48.

* cited by examiner

*Primary Examiner* — Golam M M Shameem
*Assistant Examiner* — Karen Cheng
(74) *Attorney, Agent, or Firm* — Birch, Stewart, Kolasch & Birch, LLP

(57) ABSTRACT

The present invention relates to anhydrous crystalline vinflunine salts obtained with 1 or 2 equivalents of a pharmaceutically acceptable mineral or organic acid [Acid] 1 or 2 in which [Acid] represents hydrobromic, sulfuric, lactic and fumaric acids for the group of water-soluble crystalline salts, and para-toluene sulfonic, benzoic, mandelic and para-hydroxy benzoic acids for the group of relatively insoluble crystalline salts.

9 Claims, 9 Drawing Sheets

Figure 1:
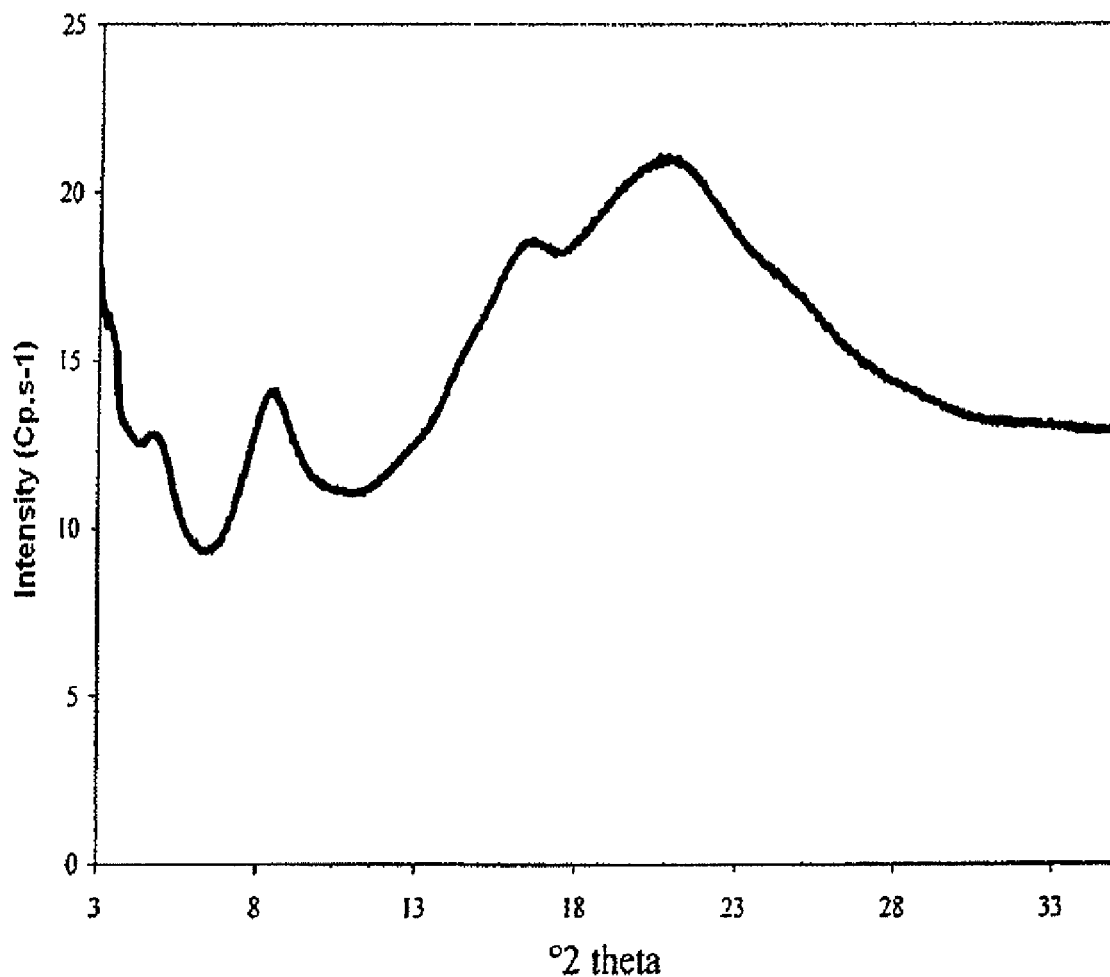

ANHYDROUS CRYSTALLINE VINFLUNINE SALTS, METHOD OF PREPARATION AND USE THEREOF AS A DRUG AND MEANS OF VINFLUNINE PURIFICATION

This application is the National Phase of PCT/EP2008/051755 filed on Feb. 13, 2008, which claims priority under 35 U.S.C. 119(e) to U.S. Provisional Application No. 60/894,127 filed on Mar. 9, 2007 and under 35 U.S.C. 119(a) to Patent Application No. 0753211 filed in France on Feb. 13, 2007, all of which are hereby expressly incorporated by reference into the present application.

The present invention relates to new salified and crystalline forms of vinflunine, methods of obtaining said forms, as well the use thereof in therapeutics.

Vinflunine is an indole derivative of the vinblastine and vincristine family.

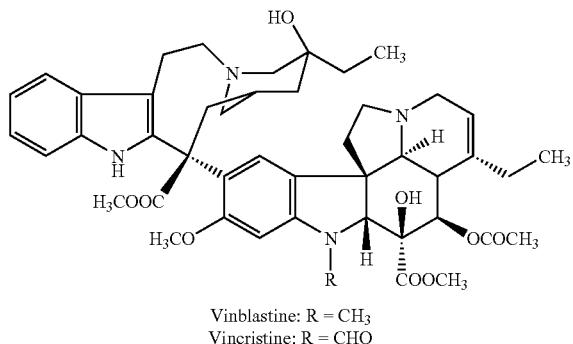

Vinblastine: R = CH$_3$
Vincristine: R = CHO

These compounds, extracts of *Catharanthus roseus*, belong to the antimitotic alkaloids and have been used for a number of years in cancer chemotherapy. The difficulties of obtaining these derivatives by extraction from plants led several research groups to identify novel similar substances having the same properties and to develop methods for the semi-synthesis thereof. Thus, vindesine and vinorelbine (Navelbine) have been obtained and marketed for the treatment of cancers. A principle character of the chemical structure of these compounds is the combination of two alkaloid monomers, namely catharanthine and vindoline.

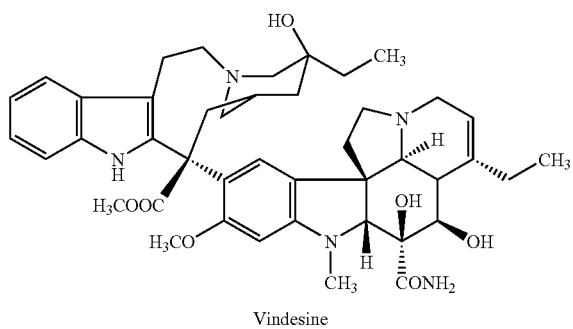

Vindesine

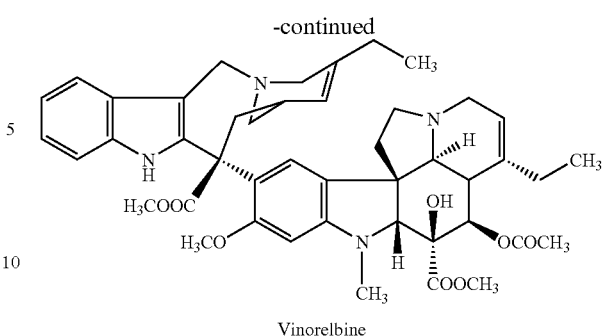

Vinorelbine

Within the framework of the development of novel synthetic routes to obtain vinorelbine, the reactivity of this compound in a superacid medium led to the identification of a novel molecule, namely 20',20'-difluoro-3',4'-dihydrovinorelbine, or vinflunine (WO95/03312). The therapeutic advantage of said compound was also verified during the same work.

The exact conformation of vinflunine has been studied by various methods of $^1$H NMR and $^{13}$C NMR spectroscopy (Magn. Reson. Chem., 2001, 39, p. 43-48). Said study was conducted on vinflunine ditartrate in solution. However, said salt has hygroscopic properties which limit its stability in a solid state, thus constituting a handicap during industrial production. To date, vinflunine ditartrate is isolated in the form of an amorphous powdery solid and must be stored at a negative temperature, lower than −15° C., and under an atmosphere of inert gas, for example under nitrogen or argon. Today, no anhydrous crystalline form of the ditartrate can be obtained, although a hydrated crystalline form of the ditartrate has been demonstrated by crystallization in hydroalcoholic solvents (patent application FR 0512942).

The handling and storage of this compound are thus delicate, and any form that improves physical stability in a solid state would make it possible to simplify the manufacturing, storage, and packaging processes.

Traditionally, the crystallization of an amorphous compound can present very great difficulties and obtaining the first crystals is always problematic. However, this type of solid form makes it possible to overcome many disadvantages of the amorphous form. Indeed, it retains less water and its stability, improved over time, facilitates its handling during industrial manufacturing processes thanks in particular to a tendency to agglomerate less in a lump, and to better flow. It also makes it possible to consider more varied galenic forms and to facilitate the manufacture and handling thereof.

Traditionally, the filterability of a crystalline suspension is greatly increased compared to a suspension of an amorphous solid.

The applicant has demonstrated that it is possible to obtain crystalline forms by using other salts, yielding anhydrous crystallized structures in a suitable solvent system. The acids tested, chosen among pharmaceutically acceptable mineral or organic acids, yielded crystalline salts whose molar ratio of the acid used to vinflunine is 1 to 1 or 2 to 1 according to the acids used. The majority of acids can yield salts which precipitate indifferently with 1 or 2 molar equivalents according to the quantity of acid used. The present invention deals with salts in crystallized forms essentially free of any molecule of water of constitution, crystallization and/or solvation. These salts will be designated throughout the present patent application under the name "anhydrous crystalline vinflunine salts."

Fumaric acid yields a salt which precipitates advantageously with a molar ratio of fumaric acid to vinflunine of 1 to 1, regardless of the quantity of acid used.

Obtaining a crystalline salt also makes it possible to open the route to techniques of purification by crystallization, which represents a considerable advantage considering the difficulties encountered during the manufacture of very high quality vinflunine.

Anhydrous crystalline vinflunine salts, obtained according to the method, can be categorized in two groups:
- mineral acid salts or organic acids of the aliphatic type, constituting a group having an advantageous water solubility for pharmaceutical use,
- aromatic organic acid salts which have low aqueous solubility but whose crystallinity presents an advantage in the development of a technique of vinflunine purification by crystallization.

Indeed, recrystallization of one of these more or less soluble salts to improve the purity of crude vinflunine can be considered. This salt can then be treated by means of a base such as, for example, sodium bicarbonate, a tertiary amine or, preferentially, ammonia, to yield a vinflunine base of better quality, which is then salified again with one of the pharmaceutically acceptable acids to yield a water-soluble salt that can be used as a drug.

This type of purification by crystallization can take place at various points in the manufacturing process such as during final purification for obtaining high quality batches or in the pre-purification of a batch, before the implementation of another refining technique such as, for example, preparative chromatography.

The applicant has demonstrated that these anhydrous crystallized salts have better stability over time, as shown it the comparative study of amorphous vinflunine ditartrate versus crystalline vinflunine fumarate reported in the text.

Thus, the present invention relates to anhydrous crystalline vinflunine salts, obtained with pharmaceutically acceptable mineral or organic acids such as, for example, in a non-exhaustive way, salts of hydrobromic, sulfuric, lactic and fumaric acids for the group of water-soluble crystalline salts, and of para-toluene sulfonic, benzoic, mandelic and para-hydroxy benzoic acids for the group of relatively insoluble crystalline salts. All of these salts can be represented in a general way by the formula (I):

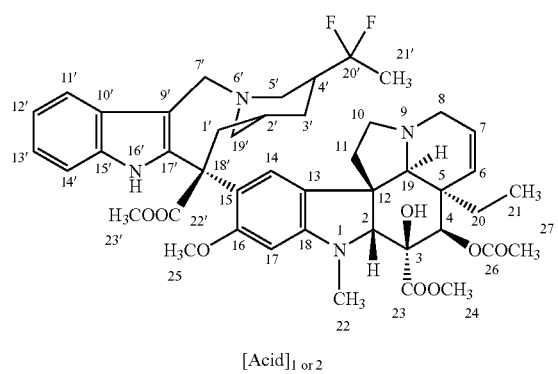

Formula (I)

in which [Acid] represents hydrobromic, sulfuric, lactic and fumaric acids for the group of water-soluble crystalline salts, and para-toluene sulfonic, benzoic, mandelic and para-hydroxy benzoic acids for the group of relatively insoluble crystalline salts.

In an advantageous way, the fumarate will be chosen in particular. Said salt is obtained rather easily, it crystallizes in an abundant manner and has the particularity of always having a molar stoichiometry of 1 molar equivalent of fumaric acid for 1 molar equivalent of vinflunine, which represents considerable advantages in terms of reproducibility, manufacturing and the mass ratio of the active product to the mass of salt.

The latter advantage is important for the preparation of oral forms such as, for example, tablets, gel caps or capsules whose composition requires large quantities of the active ingredient while avoiding increases in volume that are too large, thus making the use of this route inconvenient. Accordingly, crystalline salts, which are a more condensed form of the material than amorphous salts, also have an advantage.

The anhydrous crystalline state of salified vinflunine according to the invention is demonstrated by means of techniques known to persons skilled in the art, such as, for example, x-ray powder diffraction and infrared spectrometry, and can be verified by simple microscopy. For purposes of comparison, the powder diffractogram of the amorphous vinflunine ditartrate (not exhibiting characteristic spectral lines) is presented in FIG. 1.

The invention thus also relates to methods of preparation of crystallized vinflunine salts wherein said methods are comprised of the following steps:
- dissolution of vinflunine base in a suitable solvent;
- addition of an acid in a proportion of 1 or 2 molar equivalents, in solution or not in solution in a suitable solvent;
- evaporation of the solvent mixture;
- agitation in a liquid or a mixture of liquids, non-solvent or weakly solvent, at ambient or cooled temperature, for a period of time necessary for precipitation;
- filtration and recovery of the crystals or amorphous solids formed;
- aging by extended agitation of the amorphous solids in a liquid or a mixture of liquids, non-solvent or weakly solvent, at ambient or cooled temperature for a period of time necessary for crystallization,
- filtration and recovery of the crystals formed,
- rinsing, by means of a liquid or a mixture of liquids, non-solvent or weakly solvent, and vacuum drying the crystals.

Preferably, the solvents used to dissolve the vinflunine base are acetone, ethyl acetate and toluene. Dichloromethane or alcohols such as, for example, ethanol, methanol and 1- and 2-propanol can also be used.

Preferably, the solvents used to dissolve the acids are water, acetone, ethyl acetate and toluene. Dichloromethane or alcohols such as, for example, ethanol, methanol or 1- and 2-propanol can also be used.

Preferably, the non-solvent or weakly solvent liquids used to precipitate the salts are ethyl ether, isopropyl ether, ethyl acetate, acetone and toluene. Methyl tertiobutyl ether, hexane, heptane or petroleum ether can also be used.

Preferably, the non-solvent or weakly solvent liquids used for aging the amorphous salts are, for example, and in a nonrestrictive way, ethyl ether and isopropyl ether, ethyl acetate, acetone and toluene. Methyl tertiobutyl ether, hexane, heptane or petroleum ether can also be used.

Preferably, the non-solvent or weakly solvent liquids used for rinsing the crystals are ethyl ether and isopropyl ether. Methyl tertiobutyl ether, hexane, heptane or petroleum ether can also be used.

As indicated above, the temperature of precipitation or aging can be controlled in order to optimize the times required for, and the quality of, crystallization. Thus, advantageously a temperature lower than 50° C., more particularly a temperature between 4° C. and 25° C., will be chosen.

The quantity of solvent must be adjusted by a person skilled in the art and preferably will be between 1 and 20 parts by volume (ml) compared to the mass (g) of vinflunine.

Because of the therapeutic advantage already demonstrated for vinflunine and derivatives thereof, in particular vinflunine salts, the present invention also relates to a drug comprised of one of the crystalline vinflunine salts according to the invention. In a specific aspect, the invention relates to the use of a crystallized vinflunine salt for the preparation of a drug to be used for the treatment of cancer pathology. In particular, in a nonrestrictive way, breast, bladder, non-small cell lung and prostate cancers can be cited.

The invention also relates to a pharmaceutical composition wherein said composition contains an effective quantity of a crystallized vinflunine salt according to the invention, in a physiologically acceptable medium.

Among said pharmaceutical compositions, those which are appropriate for oral, parenteral, intravenous or subcutaneous administration, more particularly suitable for oral administration, in the form of tablets, capsules, or gel caps, can be cited more particularly.

Dosing varies according to the sex, age and weight of the patient and to the administration route.

The following examples illustrate the invention, without limiting the scope thereof.

Comparative stability of amorphous ditartrate and crystalline fumarate:

1. Raw material:
   Batch OP3.0B: amorphous vinflunine ditartrate.
   Batch JLM4008400: crystalline vinflunine fumarate.
2. Stability conditions:
   Stability studies are carried out on the powder form away from light under the following conditions:
   closed bottle: 50° C.,
   open bottle: 40° C., 75% relative humidity.
   A measurement is taken at $T_0$ and at $T_0+14$ days.
3. Analytical conditions:
   HPLC system:
   Column: Sunfire C18, 5 μm, 4.6×250 mm (Waters) temperature maintained at 35° C.
   Eluent: $CH_3CN/MeOH/H_2O/KH_2PO_4$ 400/150/450/6.8 (ml/ml/ml/g) adjusted to pH 7 (with KOH).
   Flow rate: 1 ml/min
   Detection: 269 nm
4. Results

| Batch Nature of vinflunine salt | Analysis time | Stability conditions | HPLC analysis | Water content |
|---|---|---|---|---|
| OP3.OB Amorphous ditartrate | $T_0$ | — | 99.28% | 6.27% |
|  | $T_0 + 14$ d | 50° C. | 97.18% | — |
|  |  | 40° C., 75% RH | 98.21% | 10.18% |
| JLM4008400 Crystallized fumarate | $T_0$ | — | 99.52% | 1.33% |
|  | $T_0 + 14$ d | 50° C. | 99.56% | — |
|  |  | 40° C., 75% RH | 99.38% | 4.18% |

The amorphous vinflunine ditartrate compound is degraded in powder form to a value of 2.1% at 50° C. (closed bottle) and to 1.07% in the presence of moisture (40° C., 75% RH), whereas the crystalline vinflunine fumarate, under the same conditions, remains stable (degradation less than 0.2%).

FIGURE LEGENDS

FIG. 1: Powder diffractogram of amorphous vinflunine ditartrate.

Figure 2:
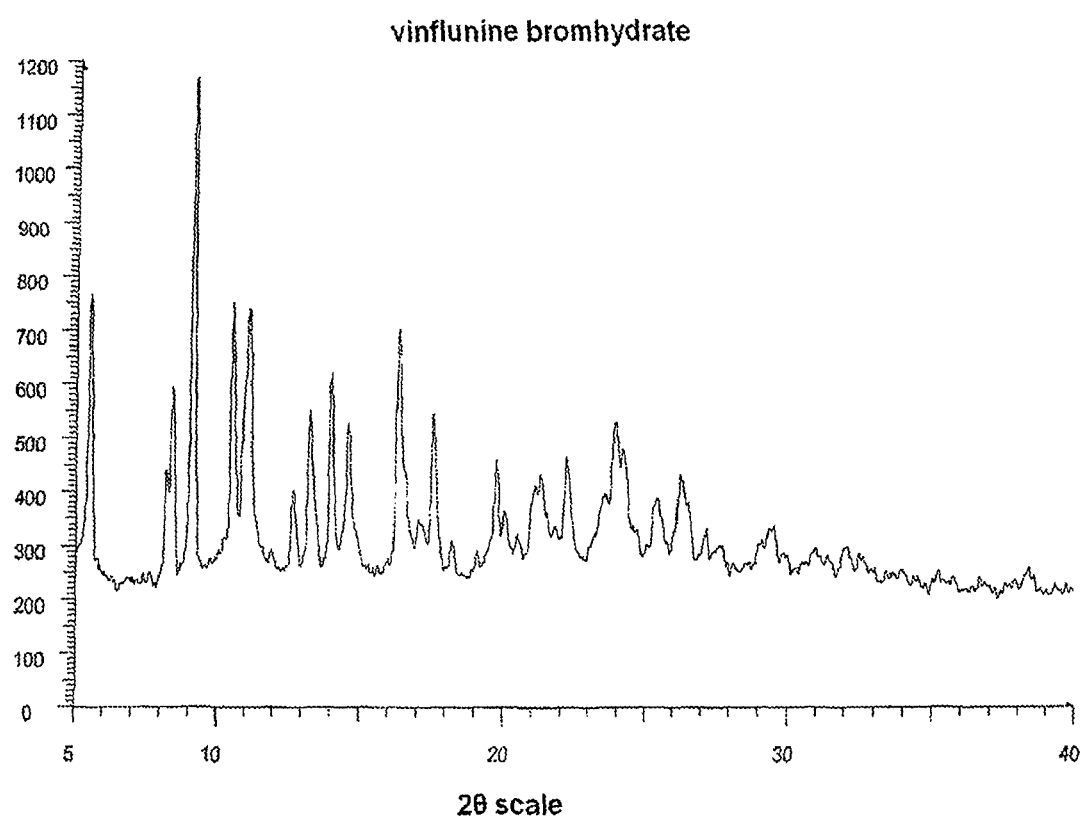
Figure 3:
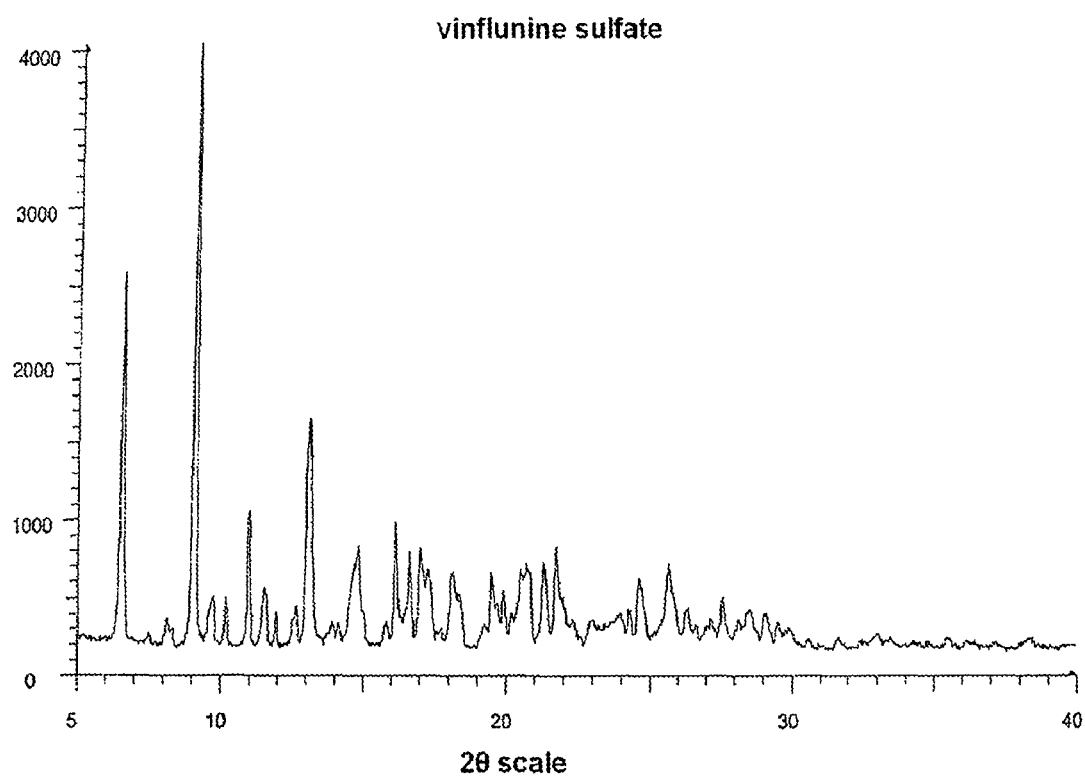
Figure 4:
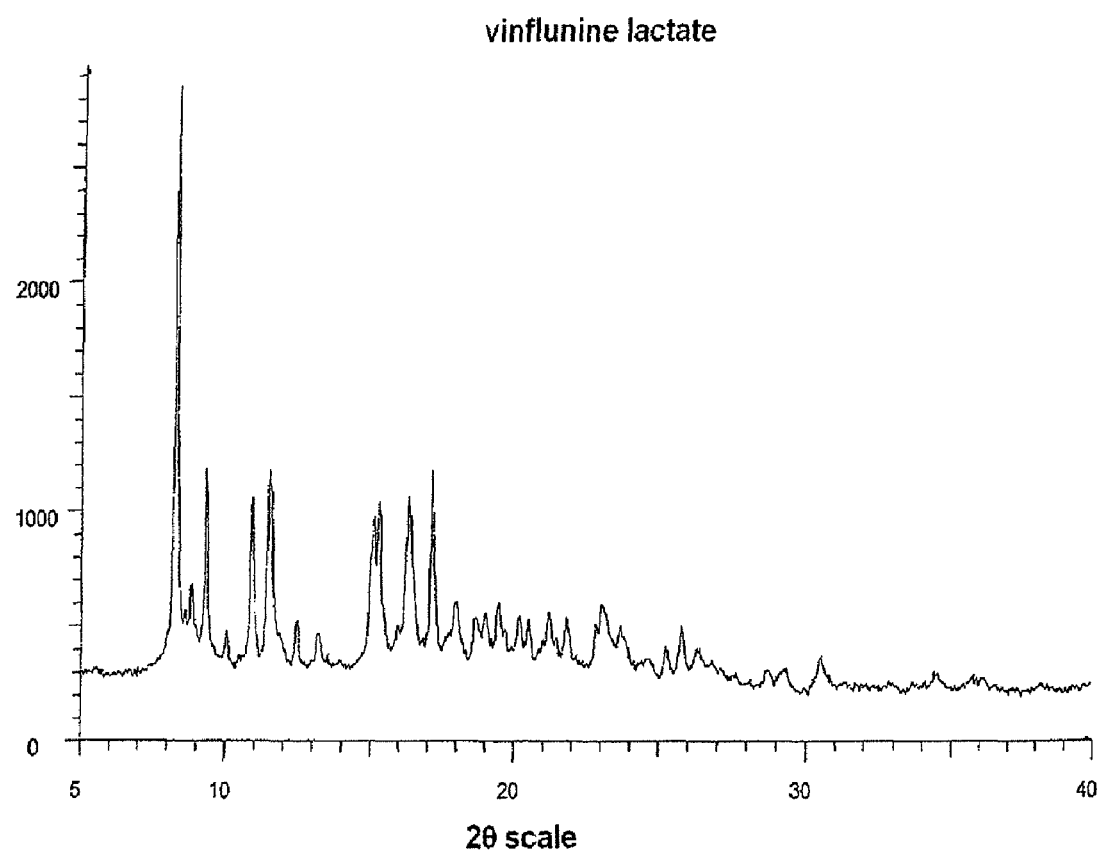
Figure 5:
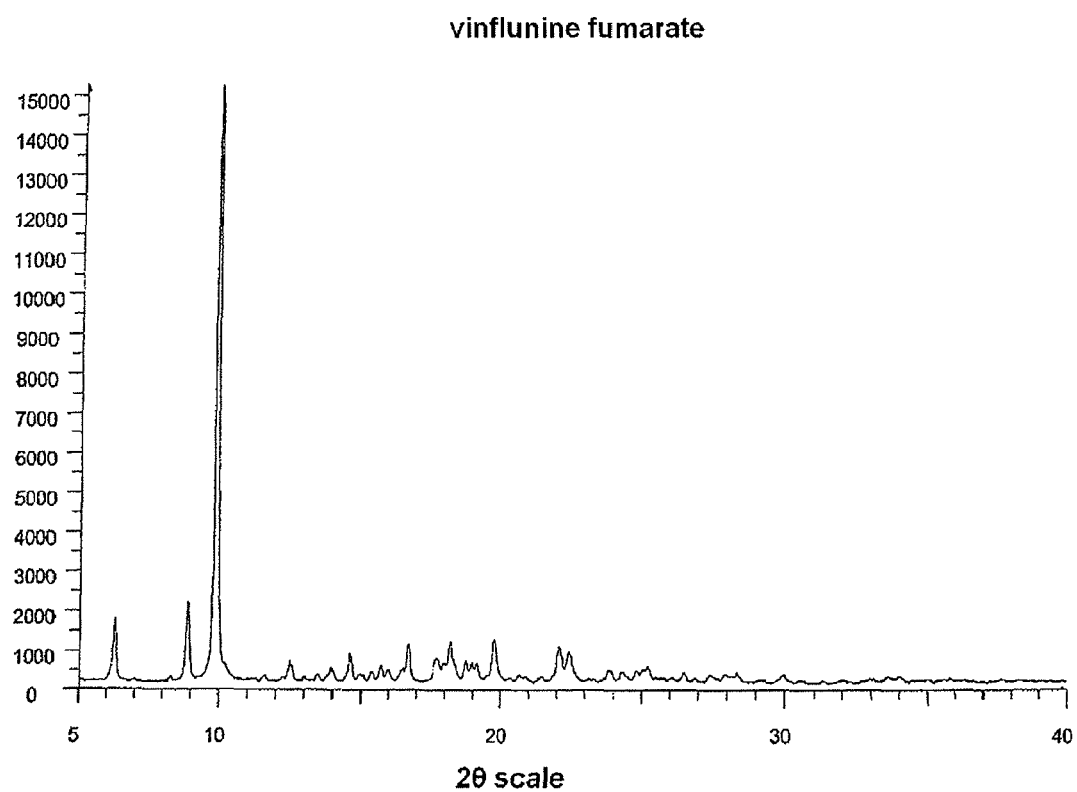
Figure 6:
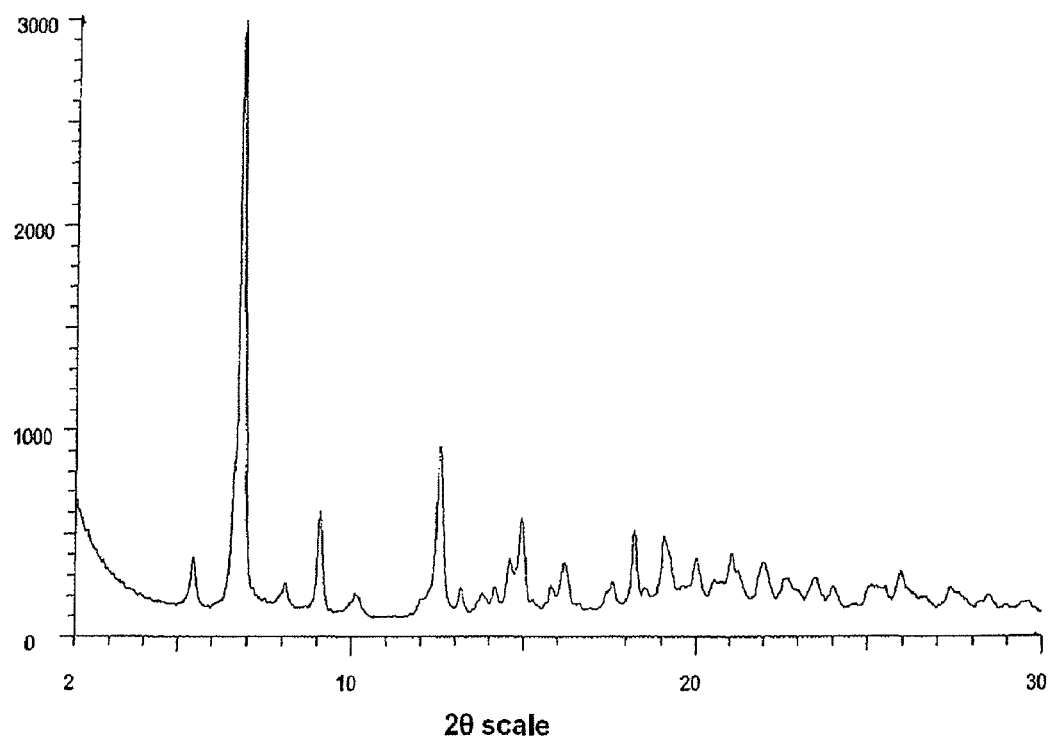
Figure 7:
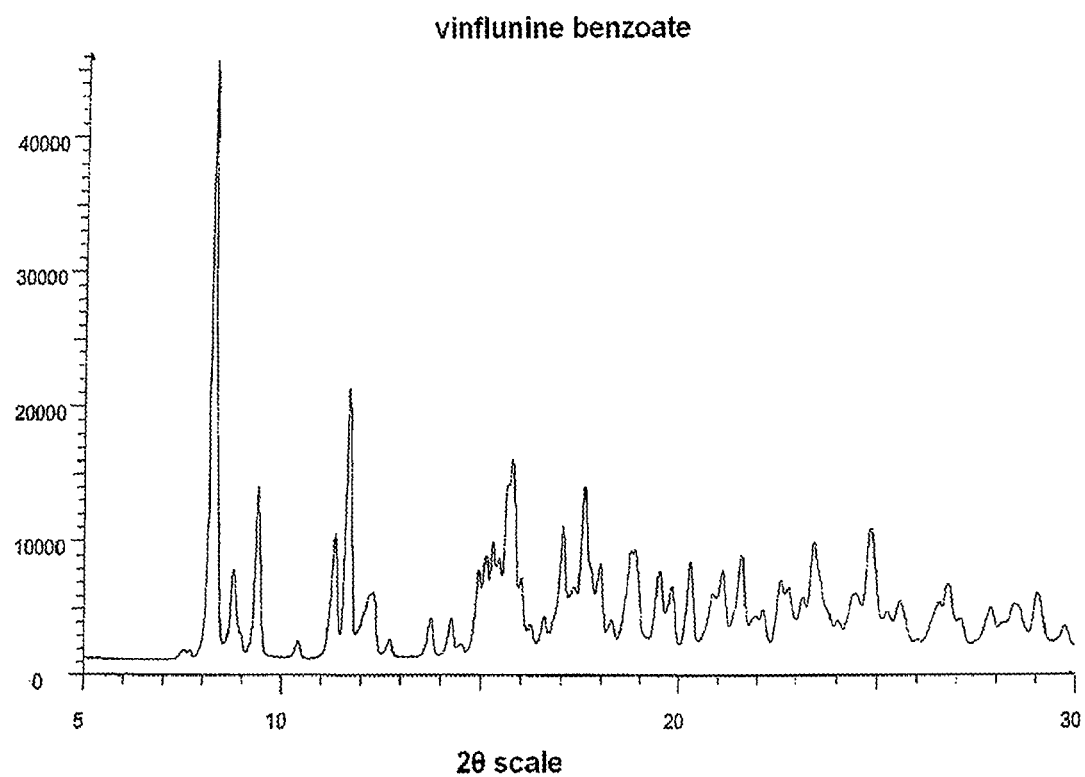
Figure 8:
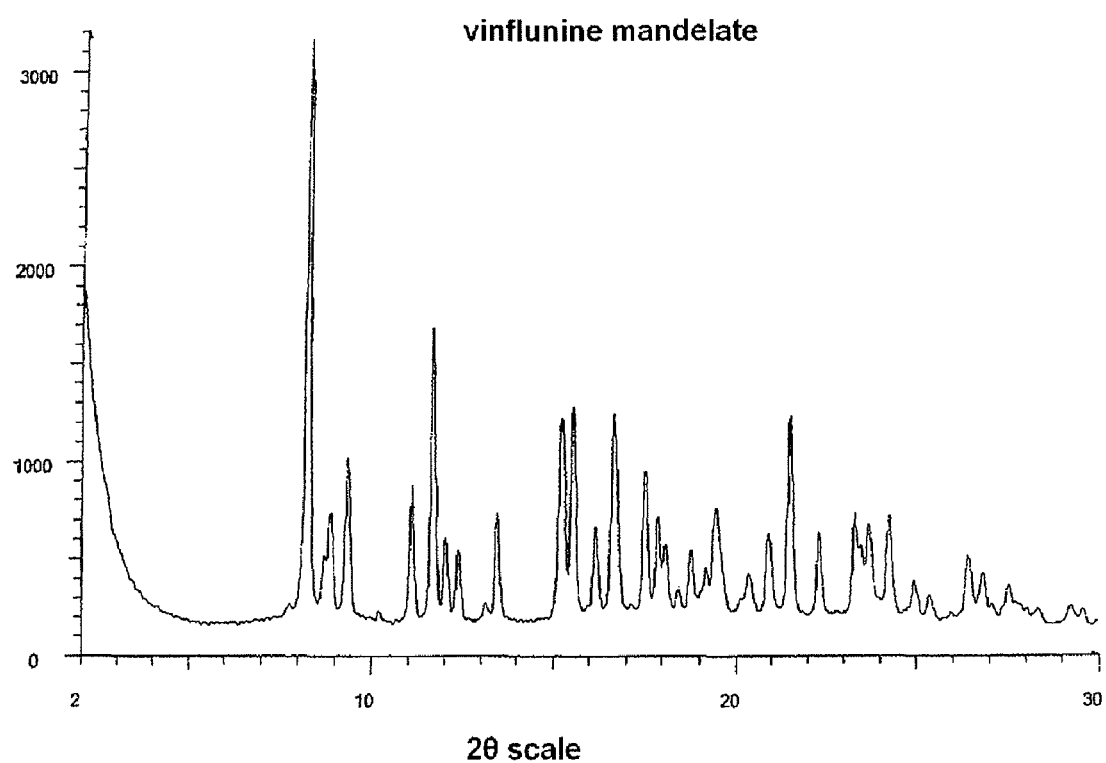
Figure 9:
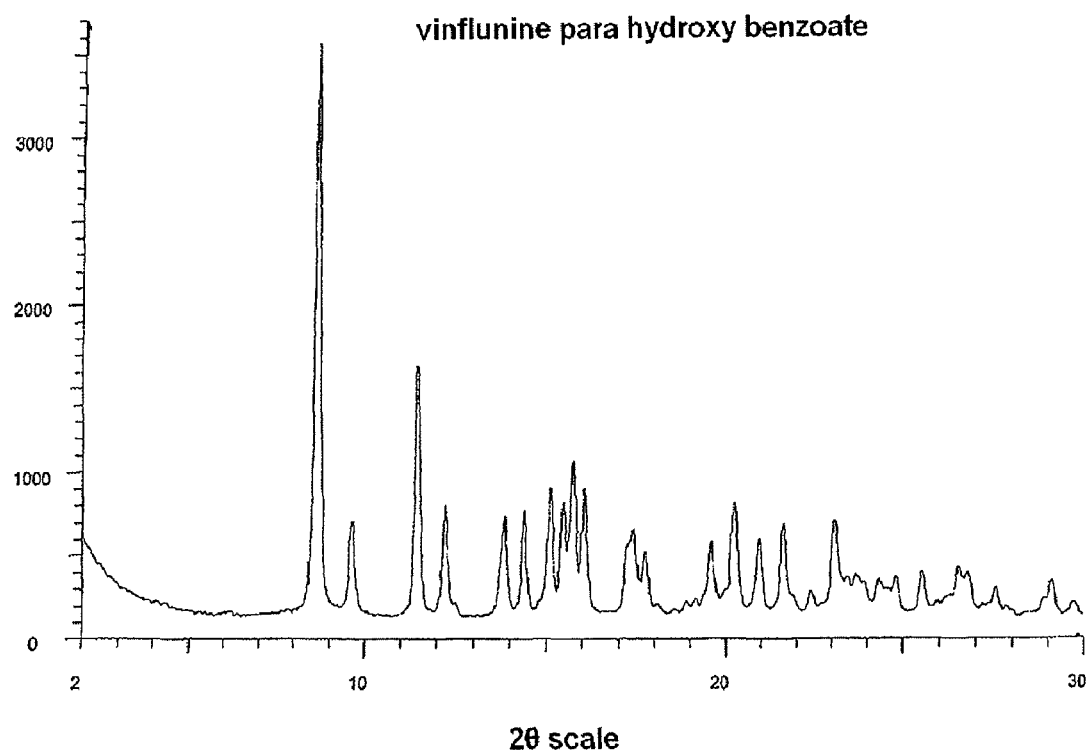

FIG. 2: Powder diffractogram of hydrobromide
FIG. 3: Powder diffractogram of sulfate
FIG. 4: Powder diffractogram of lactate
FIG. 5: Powder diffractogram of fumarate
FIG. 6: Powder diffractogram of para-toluene sulfonate
FIG. 7: Powder diffractogram of benzoate
FIG. 8: Powder diffractogram of mandelate
FIG. 9: Powder diffractogram of para-hydroxy benzoate Crystallization of Vinflunine Salts Example 1

Hydrobromide

Place a test sample of 4.56 g of vinflunine base in solution in a minimum of acetone and then add 2 equivalents of an aqueous solution of hydrobromic acid (0.53 ml for a 62% solution). The salt precipitates slowly; dilute with a little ethyl ether and allow to rest overnight. Filter and wash with ether. Dry for 20 hours under a vacuum at 70° C., away from light. 4.43 g of crystalline salt are obtained.

1H NMR (400 MHz, MeOH) δ ppm 0.72 (t, J=7.33 Hz, 3H) 1.37-1.46 (m, 1H) 1.47-1.55 (m, 1H) 1.60-1.97 (m, 4H) 1.72 (t, J=19.00 Hz, 3H) 2.04 (s, 3H) 2.12-2.22 (m, 1H) 2.65-2.77 (m, 2H) 2.75 (s, 3H) 2.81-3.20 (m, 4H) 3.33-3.44 (m, 2H) 3.54-3.65 (m, 3H) 3.64 (s, 1H) 3.77 (s, 7H) 3.87 (s, 3H) 4.87 (s, 2H) 4.93 (d, J=15.16 Hz, 1H) 5.07 (d, J=15.16 Hz, 1H) 5.31 (s, 1H) 5.42 (d, J=10.11 Hz, 1H) 5.87 (dd, J=10.11, 4.55 Hz, 1H) 6.38 (s, 2H) 7.13-7.22 (m, 2H) 7.38 (d, J=7.07 Hz, 1H) 7.72 (d, J=7.07 Hz, 1H) 10.25 (br. s., 1H)

Example 2

Sulfate

Place a test sample of 4.29 g of vinflunine base in solution in a mixture of acetone and ethanol and then add 2 equivalents of 3 M sulfuric acid (3.5 ml). Evaporate and take up the residue in acetone, add ethyl ether then allow to rest overnight; filter and wash with ether. 4.77 g of amorphous powder is obtained.

Agitate said powder for 24 hours in acetone at room temperature then add a little isopropyl ether, filter and wash with isopropyl ether. Dry under a vacuum for 20 h at 70° C., away from light. 4.53 g of crystalline product are obtained.

1H NMR (400 MHz, MeOH) δ ppm 0.73 (t, J=7.33 Hz, 3H) 1.44-1.56 (m, 2H) 1.63-1.83 (m, 2H) 1.71 (t, J=19.45 Hz, 3H) 1.89 (d, J=13.00 Hz, 1H) 1.99-2.09 (m, 1H) 2.07 (s, 3H) 2.26-2.36 (m, 1H) 2.67 (dd, J=15.66, 6.06 Hz, 1H) 2.79 (s, 3H) 2.97 (dd, J=14.40, 2.78 Hz, 1H) 3.12 (t, J=14.40 Hz, 1H) 3.30-3.35 (m, 3H) 3.34 (s, 1H) 3.40-3.51 (m, 2H) 3.71-3.82 (m, 1H) 3.72 (s, 1H) 3.76 (s, 3H) 3.81 (s, 3H) 3.85-3.94 (m, 2H) 3.88 (s, 3H) 4.88 (s, 5H) 4.94 (d, J=15.00 Hz, 1H) 5.05 (d, J=15.00 Hz, 1H) 5.31 (s, 1H) 5.64 (d, J=10.11 Hz, 1H) 5.92 (dd, J=10.11, 4.55 Hz, 1H) 6.42 (s, 1H) 6.59 (s, 1H) 7.12 (dd, J=7.33 Hz, 1H) 7.15 (dd, J=7.33 Hz, 1H) 7.37 (d, J=7.58 Hz, 1H) 7.73 (d, J=7.58 Hz, 1H) 10.41 (s, 1H)

Example 3

Lactate

Place a test sample of 4.59 g of vinflunine base in solution in a minimum of acetone and then add 2 equivalents of L(+) lactic acid (1.01 g) in solution in acetone. Evaporate the acetone and triturate in isopropyl ether then allow to rest overnight; filter and wash with isopropyl ether. 4.63 g of amorphous powder is obtained.

Agitate said powder for 24 hours in toluene at room temperature. Add a little isopropyl ether, filter and wash with isopropyl ether. Dry for 20 hours under a vacuum at 70° C., away from light. 3.81 g of crystalline product is obtained.

1H NMR (400 MHz, MeOH) δ ppm 0.70 (t, J=7.33 Hz, 3H) 1.33 (d, J=7.07 Hz, 3H) 1.36-1.49 (m, 2H) 1.60-1.81 (m, 2H) 1.70 (t, J=19.00 Hz, 3H) 1.84-1.94 (m, 1H) 1.99-2.12 (m, 1H) 2.02 (s, 3H) 2.27-2.40 (m, 1H) 2.61-2.83 (m, 4H) 2.72 (s, 3H) 3.06-3.27 (m, 6H) 3.47-3.56 (m, 1H) 3.59 (s, 1H) 3.66-3.73 (m, 1H) 3.76 (s, 6H) 3.85 (s, 3H) 4.09 (q, J=7.00 Hz, 1H) 4.87 (s, 4H) 4.92-5.03 (m, 2H) 5.25-5.35 (m, 2H) 5.84 (dd, J=10.11, 4.55 Hz, 1H) 6.28 (s, 1H) 6.35 (s, 1H) 7.13-7.23 (m, 2H) 7.36 (d, J=7.58 Hz, 1H) 7.70 (d, J=7.58 Hz, 1H)

Example 4

Fumarate

Place a test sample of 4.58 of vinflunine base in solution in a minimum of acetone and then add 1 equivalent of fumaric acid (0.65 g) in solution in methanol. Evaporate the solvents, triturate in acetone, filter and wash with ether. Dry under a vacuum for 20 hours at 70° C., away from light. 3.54 g of crystalline salt is obtained.

1H NMR (400 MHz, MeOH) δ ppm 0.71 (t, J=7.33 Hz, 3H) 1.31-1.41 (m, 1H) 1.41-1.50 (m, 1H) 1.60-1.84 (m, 3H) 1.70 (t, J=19.20 Hz, 3H) 1.89 (d, J=14.00 Hz, 1H) 1.99-2.12 (m, 1H) 2.02 (s, 3H) 2.37-2.47 (m, 1H) 2.69-2.75 (m, 6H) 2.80 (dd, J=13.89, 2.27 Hz, 1H) 3.11 (t, J=14.40 Hz, 1H) 3.17-3.39 (m, 4H) 3.55 (d, J=14.65 Hz, 1H) 3.59 (s, 1H) 3.71 (d, J=13.14 Hz, 1H) 3.76 (s, 6H) 3.86 (s, 3H) 4.87 (s, 5H) 5.00 (d, J=13.00 Hz, 1H) 5.27-5.35 (m, 2H) 5.84 (dd, J=10.11, 4.04 Hz, 1H) 6.32 (s, 1H) 6.35 (s, 1H) 6.66 (s, 2H) 7.10-7.20 (m, 2H) 7.35 (d, J=7.58 Hz, 1H) 7.70 (d, J=7.58 Hz, 1H)

Example 5

Para-Toluene Sulfonate

Place a test sample of 1.8 g of vinflunine base in solution in a minimum of acetone and then add 2 equivalents of para-toluene sulfonic acid (0.76 g) in solution in ethyl acetate. Add isopropyl ether and allow to rest overnight; filter and wash with isopropyl ether. 2.5 g of amorphous powder is obtained.

Agitate said powder for 24 hours in toluene at room temperature, filter and wash with isopropyl ether. Dry for 20 hours under a vacuum at 70° C., away from light. 1.5 g of crystalline product is obtained.

1H NMR (400 MHz, MeOH) δ ppm 0.67 (t, J=7.33 Hz, 3H) 1.45-1.55 (m, 2H) 1.58-1.83 (m, 2H) 1.71 (t, J=19.00 Hz, 3H) 1.89 (d, J=14.00 Hz, 1H) 2.02 (s, 1H) 2.05 (s, 3H) 2.19-2.30 (m, 1H) 2.35 (s, 6H) 2.67 (dd, J=15.66, 6.06 Hz, 1H) 2.78 (s, 3H) 2.92 (dd, J=14.15, 2.53 Hz, 1H) 3.03-3.44 (m, 5H) 3.54-3.64 (m, 1H) 3.59 (s, 1H) 3.68 (s, 1H) 3.72-3.82 (m, 3H) 3.76 (s, 3H) 3.79 (s, 3H) 3.87 (s, 3H) 4.87 (s, 2H) 4.93 (d, J=15.16 Hz, 1H) 5.05 (d, J=15.16 Hz, 1H) 5.29 (s, 1H) 5.55 (d, J=10.61 Hz, 1H) 5.83 (dd, J=10.11, 4.55 Hz, 1H) 6.40 (s, 1H) 6.62 (s, 1H) 7.05 (dd, J=7.33 Hz, 1H) 7.18 (dd, J=7.33 Hz, 1H) 7.18 (d, J=8.08 Hz, 4H) 7.39 (d, J=8.08 Hz, 1H) 7.57 (d, J=8.08 Hz, 4H) 7.63 (d, J=8.08 Hz, 1H) 10.43 (s, 1H)

Example 6

Benzoate

Place a test sample of 1.8 g of vinflunine base in solution in a minimum of ethyl acetate and then add 2 equivalents of benzoic acid (0.54 g) in solution in ethyl acetate. Evaporate the ethyl acetate and triturate the residue in isopropyl ether, filter and wash the precipitate with isopropyl ether. Dry under a vacuum for 20 hours at 70° C., away from light. 2.1 g of crystalline salt are obtained.

1H NMR (400 MHz, MeOH) δ ppm 0.70 (t, J=7.07 Hz, 3H) 1.30-1.40 (m, 2H) 1.54-1.92 (m, 4H) 1.68 (t, J=20.00 Hz, 3H) 2.02 (s, 3H) 2.03-2.11 (m, 1H) 2.28-2.37 (m, 1H) 2.65 (d, J=16.00 Hz, 2H) 2.64 (s, 1H) 2.71 (s, 3H) 3.02-3.29 (m, 6H) 3.50 (d, J=14.15 Hz, 1H) 3.57 (s, 1H) 3.62 (d, J=12.63 Hz, 1H) 3.75 (s, 6H) 3.85 (s, 3H) 4.78 (d, J=14.00 Hz, 1H) 4.88 (d, J=14.00 Hz, 1H) 4.87 (br. s., 2H) 5.28 (d, J=10.50 Hz, 1H) 5.30 (s, 1H) 5.82 (dd, J=10.11, 4.04 Hz, 1H) 6.32 (s, 1H) 6.34 (s, 1H) 7.07 (dd, J=7.33 Hz, 1H) 7.14 (dd, J=7.33 Hz, 1H) 7.31-7.36 (m, 2H) 7.38 (d, J=7.58 Hz, 1H) 7.45-7.47 (m, J=7.4 Hz, 1H) 7.70 (d, J=7.58 Hz, 1H) 7.92 (d, J=7.4 Hz, 2H)

Example 7

Mandelate

Place a test sample of 1.3 g of vinflunine base in solution in a minimum of acetone and then add 1 equivalent of R(−) mandelic acid (0.24 g) in solution in acetone. Evaporate the acetone under a vacuum and triturate the residue in isopropyl ether. Allow to rest overnight at room temperature, filter and wash the precipitate with isopropyl ether. Dry for 20 hours under a vacuum at 70° C., away from light. 1.3 g of crystalline salt is obtained.

1H NMR (400 MHz, MeOH) δ ppm 0.70 (t, J=7.07 Hz, 3H) 1.32-1.44 (m, 2H) 1.55-1.92 (m, 3H) 1.68 (t, J=19.00 Hz, 3H) 1.98-2.08 (m, 1H) 2.01 (s, 3H) 2.28-2.42 (m, 1H) 2.55-2.87 (m, 3H) 2.67 (s, 1H) 2.72 (s, 3H) 3.00-3.29 (m, 6H) 3.60 (s, 2H) 3.57 (s, 1H) 3.75 (s, 6H) 3.85 (s, 3H) 4.89 (s, 3H) 4.88 (s, 4H) 5.28 (d, J=10.00 Hz, 1H) 5.29 (s, 1H) 5.82 (dd, J=9.60, 4.04 Hz, 1H) 6.33 (s, 2H) 7.09 (t, J=7.58 Hz, 1H) 7.16 (t, J=7.58 Hz, 1H) 7.20-7.30 (m, 3H) 7.34 (d, J=8.08 Hz, 1H) 7.43 (d, J=7.07 Hz, 2H) 7.67 (d, J=8.08 Hz, 1H)

Example 8

Para-Hydroxy Benzoate

Place a test sample of 1.3 g of vinflunine base in solution in a minimum of acetone and then add 1 equivalent of para-hydroxy benzoic acid (0.22 g) in solution in acetone. Evaporate the acetone under a vacuum and triturate the residue in isopropyl ether. Allow to rest overnight at room temperature, filter and wash the precipitate with isopropyl ether. Dry for 20 hours under a vacuum at 70° C., away from light. 1.3 g of crystalline salt is obtained.

1H NMR (400 MHz, MeOH) δ ppm 0.71 (t, J=7.07 Hz, 3H) 1.29-1.40 (m, 2H) 1.56-1.92 (m, 3H) 1.67 (t, J=19.20 Hz, 3H) 1.98-2.08 (m, 1H) 2.01 (s, 3H) 2.28-2.38 (m, 1H) 2.53-2.76 (m, 2H) 2.65 (s, 1H) 2.71 (s, 3H) 3.00-3.28 (m, 7H) 3.49 (d, J=13.64 Hz, 1H) 3.58 (d, J=10.00 Hz, 1H) 3.57 (s, 1H) 3.75 (s, 6H) 3.84 (s, 3H) 4.76 (d, J=14.00 Hz, 1H) 4.84 (d, J=15.00 Hz, 1H) 4.89 (s, 4H) 5.28 (d, J=14.00 Hz, 1H) 5.30 (s, 1H) 5.82 (dd, J=9.60, 4.04 Hz, 1H) 6.34 (s, 2H) 6.74 (d, J=8.59 Hz, 2H) 7.06 (dd, J=7.33 Hz, 1H) 7.12 (dd, J=7.33 Hz, 1H) 7.31 (d, J=8.08 Hz, 1H) 7.70 (d, J=7.58 Hz, 1H) 7.79 (d, J=8.08 Hz, 2H)

Nuclear Magnetic Resonance:

The $^1$H NMR spectrum is recorded at the nominal frequency of 400 MHz on a Bruker Avance DPX 400 spectrometer equipped with a broad band inverse probe and a z-gradient accessory. Before the recording of the NMR spectrum, the product is solubilized in deuterated methanol (Euriso-top, item D 324-B, batch A-3561) at an approximate concentration of 0.4% (w/v). Chemical shifts are expressed in ppm compared to TMS (tetramethylsilane) used as the internal standard. Coupling constants are expressed in hertz.

Nuclear magnetic resonance is used to confirm the structural integrity of the vinflunine salt molecule after the crystallization study as well as to determine the molar ratio of the acid used to vinflunine. This ratio is 1 to 1 or 2 to 1 according to the acids used.

X-Ray Powder Diffraction:

The samples were analyzed on a Bruker AXS D8 Advance diffractometer equipped with a copper anticathode ($\lambda$=1.54060 Å) operating at 30 kV and 53 mA, a variable primary slit block and a Vantec detector.

The analyses were carried out between 2 and 40°2θ with a step of 0.007°2θ and a counting time of 40 s. The samples were placed in a zero-reflection sample holder (C79298-A3158-B188 Bruker AXS).

The invention claimed is:

1. Anhydrous crystalline vinflunine salts obtained with 1 or 2 equivalents of a pharmaceutically acceptable mineral or organic acid.

2. Anhydrous crystalline salts according to claim 1, wherein said salts are selected among fumarate, bromhydrate, sulfate, lactate, para-toluene sulfonate, benzoate, mandelate and para-hydroxy benzoate.

3. A method of preparation of anhydrous crystalline vinflunine salts according to claim 1 comprised of the following steps:
   dissolution of vinflunine base in a suitable solvent or a mixture of solvents;
   addition of 1 or 2 molar equivalents of a mineral or organic acid for 1 molar equivalent of vinflunine;
   precipitation of the salt;
   filtration and recovery of the salt formed;
   aging and crystallization of the salt in a solvent or non-solvent,
   filtration, rinsing and vacuum drying of the crystals.

4. A method of preparation according to claim 3, wherein the vinflunine base is dissolved in a solvent or in a mixture of solvents chosen among acetone, ethyl acetate, ether, toluene, dichloromethane, methanol, ethanol, 1-propanol and 2-propanol.

5. A method of preparation according to claim 3, wherein the mineral or organic acid is selected from hydrobromic, sulfuric, lactic, fumaric, para-toluene sulfonic, benzoic, mandelic, and para-hydroxy benzoic acid.

6. A method of preparation according to claim 3, wherein the acids are placed in solution in water, an alcohol, or a suitable organic solvent.

7. A method of preparation according to claim 3, wherein precipitation of the salt is carried out in the medium or in a solvent or a solvent/non-solvent mixture selected from acetone, ethyl acetate, ether, isopropyl ether, toluene, hexane, heptane, cyclohexane or petroleum ether.

8. A method of preparation according to claim 3, wherein aging is carried out in a solvent or a solvent/non-solvent mixture selected from acetone, ethyl acetate, ether, isopropyl ether, toluene, hexane, heptane, cyclohexane or petroleum ether.

9. A pharmaceutical composition comprising an anhydrous crystalline vinflunine salt according to claim 1 in a physiologically acceptable medium.

* * * * *